United States Patent [19]

Azema et al.

[11] Patent Number: 4,902,122

[45] Date of Patent: Feb. 20, 1990

[54] OPTICAL SYSTEM FOR DETERMINING THE VARIATION OF CURVATURE OF AN OBJECT ON A ZONE OF SMALL DIMENSIONS

[75] Inventors: Alain Azema; Jean Botineau; Gérard Moulin, all of Nice, France

[73] Assignee: Synthelabo, Paris, France

[21] Appl. No.: 213,122

[22] Filed: Jun. 29, 1988

[30] Foreign Application Priority Data

Sep. 4, 1987 [FR] France ................................. 87 12302

[51] Int. Cl.⁴ ............................................... A61B 3/10
[52] U.S. Cl. .......................................... 351/212; 356/2
[58] Field of Search .................... 351/212, 221; 356/2, 356/273; 128/303.1

[56] References Cited

U.S. PATENT DOCUMENTS

| | | |
|---|---|---|
| 3,096,767 | 7/1963 | Gresser . |
| 3,704,176 | 11/1972 | Vassiliadis et al. . |
| 3,720,213 | 3/1973 | Hobart et al. . |
| 3,769,963 | 11/1973 | Goldman . |
| 3,796,220 | 3/1974 | Bredemeir . |
| 3,821,510 | 6/1974 | Muncheryan . |
| 3,930,504 | 1/1976 | de LaForcade . |
| 4,165,744 | 8/1979 | Cravy et al. . |
| 4,209,252 | 6/1980 | Arditty et al. ........................... 356/4 |
| 4,346,991 | 8/1982 | Gardner et al. .................... 351/221 |
| 4,397,310 | 8/1983 | Pomerantzeff . |
| 4,461,294 | 7/1984 | Baron . |
| 4,648,400 | 3/1987 | Schneider et al. . |
| 4,665,913 | 5/1987 | L'Esperance, Jr. . |
| 4,729,372 | 3/1988 | L'Esperance, Jr. . |

FOREIGN PATENT DOCUMENTS

| | | |
|---|---|---|
| 3148748 | 7/1983 | Fed. Rep. of Germany . |
| 215698 | 11/1984 | German Democratic Rep. . |
| 58-193408 | 11/1983 | Japan . |
| WO86/02249 | 4/1986 | PCT Int'l Appl. . |
| 929097 | 5/1982 | U.S.S.R. . |
| 975011 | 11/1982 | U.S.S.R. . |
| 1209451 | 10/1970 | United Kingdom . |

OTHER PUBLICATIONS

Trokel et al., American Journal of Opthalmology, vol. 96, No. 6, (Dec. 6, 1983) pp. 710–715.
European Published Pat. Appln. 0111060 (Jun. 20, 1984).
Taboada et al., Health Physics, vol. 40 (May 1981), pp. 677–683.
European Published Pat. Appln. No. 0151869 (Aug. 21, 1985).
Patent Abstracts of Japan, vol. 7, No. 188 (Aug. 17, 1983), p. 217 (1333).
European Published Patent Application No. 0,207,648 (Jan. 7, 1987).
European Published Patent Application No. 0,224,3222 (Jun. 3, 1987).
European Published Patent Application No. 0,191,688 (Aug. 20, 1986).

Primary Examiner—P. M. Dzierzynski
Attorney, Agent, or Firm—Fisher, Christen & Sabol

[57] ABSTRACT

This invention relates to an optical system for determining the curvature or the modification of curvature of an object on a zone of small dimensions, wherein it comprises: a light source; first optics adapted to form a parallel light beam from the beam emitted by said source; a semireflecting element disposed on the path of said parallel beam; second focussing optics receiving the parallel beam reflected by said element and being capable of moving parallel to the direction of propagation of said light beam, so that their image focus merges with the center of curvature or the surface of said object; third focussing optics receiving the beam reflected by the object, and means for detecting the image formed by said system. The invention is more particularly applicable in keratometry.

10 Claims, 2 Drawing Sheets

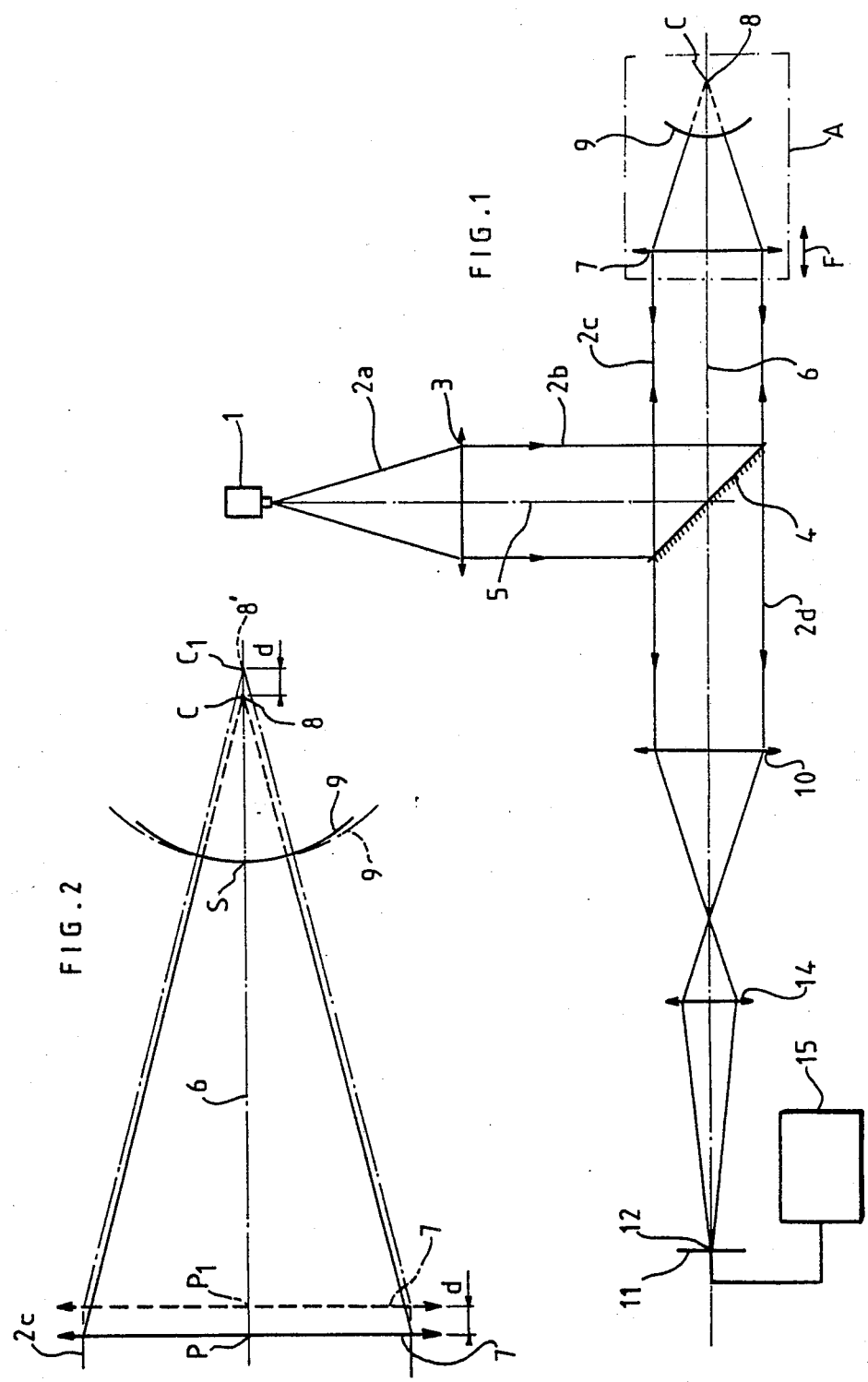

OPTICAL SYSTEM FOR DETERMINING THE VARIATION OF CURVATURE OF AN OBJECT ON A ZONE OF SMALL DIMENSIONS

BACKGROUND OF THE INVENTION

The present invention relates to an optical system for determining the curvature or modification made to the curvature of an object.

The invention is applicable, more particularly but not exclusively, to determining the variation of curvature of the cornea of the eye, in its central zone, during a surgical treatment thereof, particularly by photoablation, with the aid for example of the apparatus described in document EP-A No. 0 191 688, and especially adapted for the treatment of zones not exceeding some millimeters diameter.

Such a surgical apparatus is intended to modify the curvature of the cornea by photodecomposition of the corneal matter. In fact, it is known that certain disorders, such as myopia, hypermetropia and astigmatism, may be treated by modification of the curvature of the cornea.

During such surgical treatment, it is essential to be able to determine, precisely, reliably and rapidly, the variation during treatment of the curvature of the central zone of the cornea in order, at each elementary step of the treatment, on the one hand, to measure the effective ablation of corneal matter during said step and, on the other hand, to modulate, as a function of said ablation, the amplitude of the following step, it being understood that it is crucial not to exceed, at the end of treatment, a predetermined modification of curvature.

SUMMARY OF THE INVENTION

To that end, the present invention relates to an optical system for determining, precisely, reliably and rapidly, the modification of curvature of the cornea during surgical treatment and, more generally, that of an object whose curvature must undergo modifications.

To that end, the optical system for determining the variation of curvature of an object is noteworthy, according to the invention, in that it comprises:
a light source;
first optics adapted to form a parallel light beam from the beam emitted by said source;
a semi-reflecting element disposed on the path of said parallel beam;
second focussing optics receiving the parallel beam reflected by said element and being capable of moving parallel to the direction of propagation of said light beam reflected by said element, so that their image focus merges at least substantially with the centre of curvature or the surface of said object, this latter reflecting the light beam in the direction of said second optics so as to form a beam addressed to said semi-reflecting element;
third focussing optics receiving said beam coming from said element, and
means for detecting the image formed by said system, disposed beyond said third optics in the direction of propagation of the reflected beam.

It is seen that, in the optical system of the invention, the arrangements of the light source and of the detection means are interchangeable.

According to a first mode of operation (keratometry), said second focussing optics are placed in two positions such that their image focus merges successively with the centre of curvature of the object and with the surface of the object, the adjustments being effected by the best adjustment of the image. The displacement of the second optics between these two positions provides the value of the radius of curvature (and possibly of the astigmatism of the surface measured).

According to a second mode of operation (differential keratometry), if said second focussing optics are initially placed so that their image focus merges with the centre of curvature of the object (best adjustment of the image), and if this latter undergoes a modification of curvature, the second optics may then be displaced until the image focus thereof merges with the new centre of curvature of the object (clear image), and measurement of this displacement will enable the corresponding modification of curvature of the object to be determined.

According to a third mode of operation (likewise in differential keratometry), the second optics are maintained in fixed position, the modification of curvature being attained by analysis of the deformation of the spot at the level of the detection means.

According to another feature of the invention, said detection means may comprise a linear array or a mosaic of photodiodes.

According to further features of the invention, said first optics may be constituted by a collimator lens, said second focussing optics may be a focussing lens and said third focussing optics may be a lens or an association of lenses intended to obtain an image corresponding to an enlargement adapted to the dimension of the detection means.

Moreover, said light source may be constituted by a laser diode or an electroluminescent diode, possibly associated with an optical fiber.

Furthermore, means for displaying the image formed by the system may be associated with said detection means.

BRIEF DESCRIPTION OF THE DRAWING FIGURES

The invention will be more readily understood on reading the following description with reference to the accompanying drawings, in which:

FIG. 1 is a schematic view of the optical system according to the invention.

FIG. 2 is an enlarged view of zone A of FIG. 1, illustrating the operation of the system of the invention.

DETAILED DESCRIPTION OF THE PREFERRED EMBODIMENTS

Figure 3:
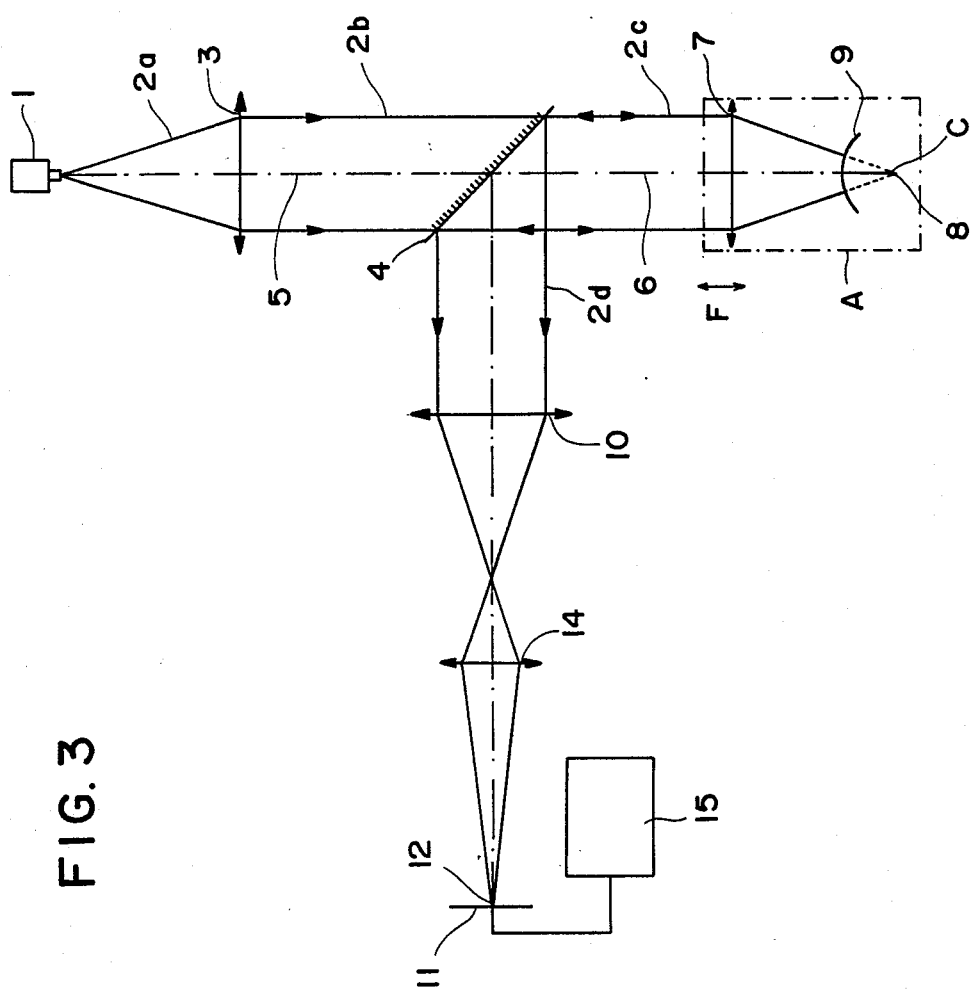
FIG. 3 is a schematic view of an alternate embodiment of the optical system according to the invention.

Referring now to the drawings, the optical system of the invention, in order to determine the variation of curvature of an object, particularly an ocular cornea during surgical treatment for correcting the curvature thereof, for example by photodecomposition, comprises a source 1 capable of emitting a light beam 2a. Essentially for reasons of energetic order and also in order easily to obtain a punctual source, it is advantageous to use as light source a laser diode or an electroluminescent diode, possibly coupled with an optical fiber.

The optical system then comprises first optics 3, constituted for example by a collimator lens intended to form a parallel light beam 2b from the beam 2a emitted by the source 1.

A semi-reflecting mirror 4 is disposed on the path of the parallel beam 2b. The mirror 4 is inclined, in this embodiment, at 45° with respect to the optical axis 5 of the light beam 2b received by the mirror 4, with the result that the optical axis 6 of the beam 2c reflected by the mirror 4 is perpendicular to the optical axis 5 of the beam 2b received by the mirror 4.

Second focussing optics 7, constituted for example by a focussing lens, receive the parallel beam 2c reflected by the mirror 4 and is capable of moving, parallel to the direction of propagation of the light beam 2c reflected by the mirror 4 (double arrow F), so that their image focus 8 merges at least substantially with the centre of curvature C of the object 9. This latter reflects the light beam 2c in the direction of the lens 7 so as to form a beam 2d passing through the mirror 4.

Third focussing optics, constituted, in the example shown, by a focussing lens 10 and a microscope lens 14, receive the beam 2d having traversed in the mirror 4, and detection means 11 are provided beyond the third optics 10, in the direction of propagation of the reflected beam 2d, to detect the image 12 formed by the system. In the example shown, the detection means 11 are constituted by a linear array of photodiodes. Furthermore, means 15 for displaying the image formed by the system may be associated with the detection means 11. It will be noted that the arrangements of elements 1-2a 3-2b-5 and 2d-10-14-12-15 may be interchanged (as shown in FIG. 3).

Operation of the optical system according to the invention will be described hereinafter, with more particular reference to FIG. 2.

In a first mode of operation (keratometry), the lens 7 lies at a certain position P along the optical axis 6 for which the image focus 8 of the lens 7 merges with the centre of curvature C of the object 9. In this position of the lens 7, the object 9 reflects the beam 2c in a parallel beam 2d identical to the preceding one except for the direction of propagation of light, with the result that the optimum adjustment of the image 12 formed by the system on the linear array 13 of photodiodes is obtained. This optimum adjustment is translated by the illumination of a minimum number of photodiodes, indicated by the display means 15. For another position Ps of the lens 7 (not shown) along the optical axis 6, the image focus 8 of the lens 7 merges with the summit S of the object 9, which again corresponds to a clear image on the detector 11. The distance between points P and P' gives the radius of curvature of the object 9 at point S. If object 9 is not spherical at S, its astigmatism may be measured by the deviation between the two points P' and P" corresponding to the optimum adjustment on the principal centres of curvature.

In a second mode of operation (differential keratometry), the adjustment of the lens 7 is started, as hereinabove, at point P corresponding to the centre of curvature of the object 9 at point S. When the object 9 undergoes a modification of curvature (in FIG. 2, it has been assumed that the summit S was conserved), the image formed by the system is modified, which may be read on the display means. The operator will then displace the lens 7 so as to tend towards the illumination of a minimum of photodiodes indicated hereinabove. The position P1 of the lens 7 corresponding to this minimum illumination will be such that the image focus 8 thereof coincides with the new centre of curvature C1 of the object 9. The variation of the curvature of the object 9 is determined by measuring the corresponding displacement d of the lens 7 (i.e., the distance between P and $P_1$).

According to a third mode of operation (likewise in differential keratometry), the lens 7 is adjusted in fixed manner at point P or at point P1. The variation of curvature is then deduced from the deformation of the spot on the detector.

The displacement of the lens 7 may be effected manually, or with the aid of drive means (not shown) possibly coupled with means for detecting the image and capable of controlling the displacement of the lens, for a better adjustment of the image, as a function of the image detected.

The optical system of the invention, known under the name of "keratometer", may be integrated in a surgical apparatus for modifying the curvature of the cornea of the eye. The data furnished by the keratometer make it possible, after processing on a computer, in particular to modulate the amplitude of the following elementary step of treatment as a function of the results thus measured of the preceding step.

What is claimed is:

1. An optical system for determining the curvature or the variation of curvature of an object (9) in a zone of small diameter, comprising:
   (a) a light source (1);
   (b) first optical means (3) for forming a first parallel light beam (2b) from the beam emitted by said source;
   (c) a semi-reflecting element (4) disposed on the path of said first parallel light beam and transmitting a second parallel light beam (2c);
   (d) second optical means (7) for focusing said second parallel light beam (2c), said second optical means (7) being movable parallel to the direction of propagation of said second light beam and having an image focus (8) which may be brought to merge at least substantially with the center of curvature (C) or the surface (S) of said object (9), said object (9) reflecting the light beam focused by said second optical means, in the direction of said second optical means (7) which forms a third light beam (2d) addressed to said semi-reflecting element (4);
   (e) third optical means (10) receiving said third light beam (2d) coming from said semi-reflecting element (4) and focussing said third light beam (2d) for forming an image (12) of said object (9); means for detecting (11) said image and
   (f) means (15) for displaying said image (12), said second optical means (7) being moved in order that said image (12) on said displaying means be clear.

2. The optical system of claim 1, wherein said detection means are constituted by assemblies of photodiodes.

3. The optical system of claim 2, wherein said third focussing optics are associated with fourth focussing optics disposed between said third focussing optics and said assembly of photodiodes, thus allowing the formation of an image of dimension adapted to that of the assembly of photodiodes.

4. The optical system of claim 1, wherein said second and third focussing optics are focussing lenses.

5. The optical system of claim 1, wherein said first optics are constituted by a collimator lens.

6. The optical system of claim 1, wherein said light source is constituted by a laser diode.

7. The optical system of claim 6, wherein said laser diode is operatively connected to an optical fiber.

8. The optical system of claim 1, wherein means for displaying the image formed by the system are associated with said detection means.

9. The optical system of claim 1, wherein said light source comprises an electroluminescent diode.

10. The optical system of claim 9, wherein said electroluminescent diode is operatively connected with an optical fiber.

* * * * *